United States Patent [19]

Dailey et al.

[11] Patent Number: 4,803,563
[45] Date of Patent: Feb. 7, 1989

[54] ROTOR-IN-STATOR EXAMINATION MAGNETIC CARRIAGE AND POSITIONING APPARATUS

[75] Inventors: George F. Dailey, Plum Borough; Paul E. Morrison, Trafford, both of Pa.

[73] Assignee: Westinghouse Electric Corp., Pittsburgh, Pa.

[21] Appl. No.: 92,790

[22] Filed: Sep. 2, 1987

[51] Int. Cl.$^4$ .............................................. H06N 7/18
[52] U.S. Cl. ..................................... 358/100; 358/101; 358/107; 324/220; 324/221; 324/262
[58] Field of Search ............... 358/100, 108, 101, 107; 324/220, 221, 226, 262; 280/652

[56] References Cited

U.S. PATENT DOCUMENTS

| | | | |
|---|---|---|---|
| 4,139,822 | 2/1979 | Urich et al. | 324/219 |
| 4,171,139 | 10/1979 | Cockram | 280/652 |
| 4,201,746 | 5/1980 | Burd et al. | 285/9.1 |
| 4,272,781 | 6/1981 | Taguchi et al. | 358/100 |
| 4,368,642 | 1/1983 | Carodiskey | 73/623 |
| 4,502,331 | 3/1985 | Singh et al. | 73/627 |
| 4,560,931 | 12/1985 | Murakami et al. | 324/220 |
| 4,591,284 | 5/1986 | Lim et al. | 400/691 |
| 4,629,984 | 12/1986 | Scalese | 324/228 |
| 4,709,582 | 12/1987 | Besanceney | 73/611 |
| 4,722,001 | 1/1988 | Röhrich et al. | 358/100 |

FOREIGN PATENT DOCUMENTS

| | | |
|---|---|---|
| 2492527 | 4/1982 | France . |
| 627393 | 8/1978 | U.S.S.R. . |

OTHER PUBLICATIONS

Paper presented at EPRI Conference, Sep. 1986, San Antonio, Tex., entitled "Remote Inspection of Steam Turbine Blades".

Primary Examiner—James J. Groody
Assistant Examiner—John K. Peng

[57] ABSTRACT

A moveable magnetic carriage on which is mounted inspection equipment for inspecting the stator of an electrical generator without removal of the generator rotor. An associated positioning device positions the carriage on the generator.

19 Claims, 3 Drawing Sheets

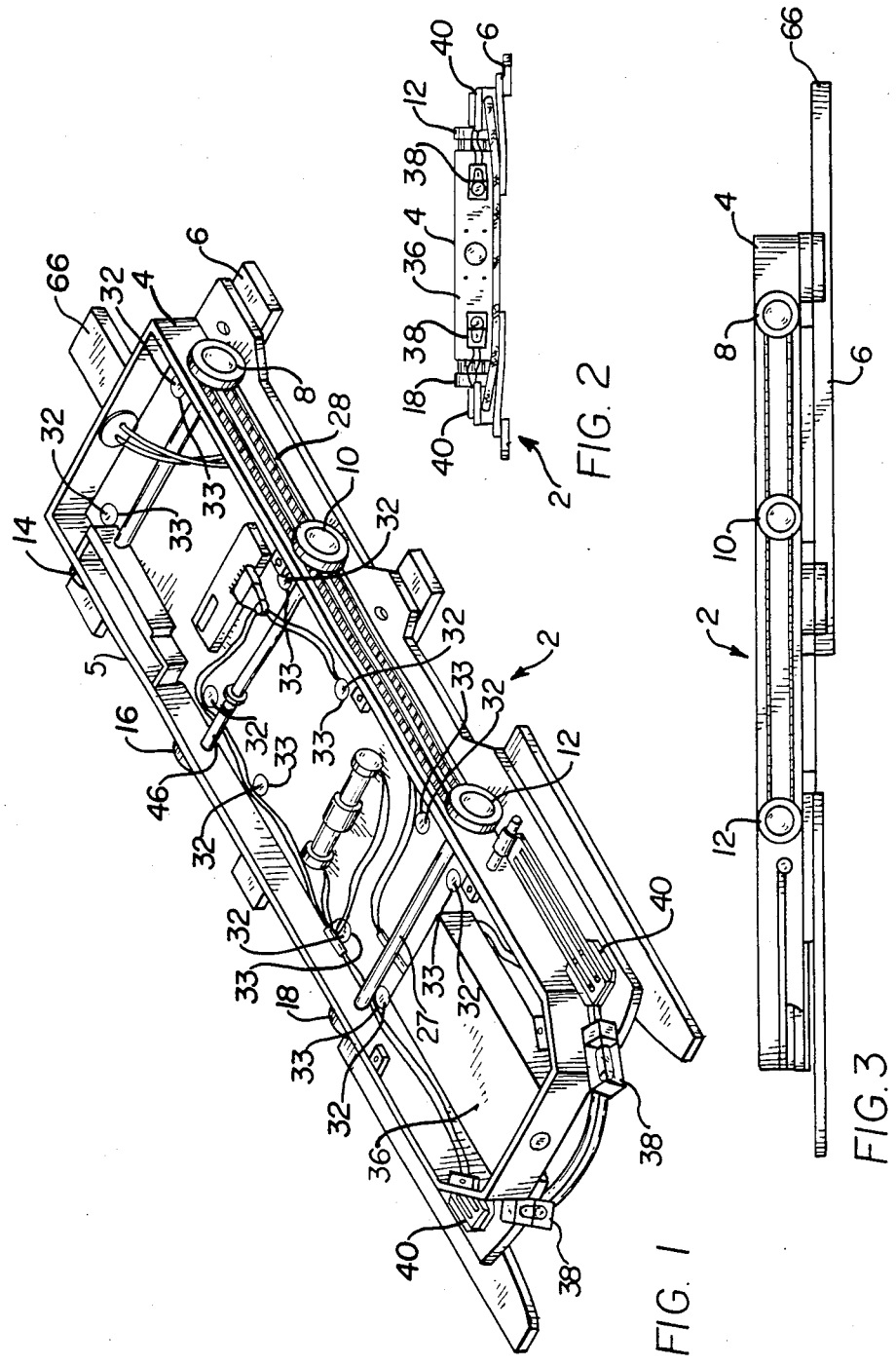

ROTOR-IN-STATOR EXAMINATION MAGNETIC CARRIAGE AND POSITIONING APPARATUS

BACKGROUND OF THE INVENTION

1. Field of the Invention

The present invention pertains to a carriage for positioning inspection apparatus within an electrical generator.

2. Background Information

The stator cores of turbo-generators and other electrical machines are built up of electrical grade steel laminations, each of which is coated with a thin layer of electrical insulation. This insulation prevents the 60 HZ alternating magnetic flux in the stator core from inducing eddy currents between laminations. In most turbo-generators, the laminations are electrically connected together at their outside diameter where they are supported by the stator frame. However, if the insulation is defective near the stator bore, a conducting path is formed through which currents are induced by the alternating flux. The heating from the induced currents is highest at the defective insulation contact points between laminations where current density is increased. These damaged regions may become hot in service and such regions are, typically, identified as "hot spots". Hot spots can also occur in generators in which the laminations are electrically insulated from the stator frame. In this case the electrical circuit is usually completed through defective interlaminar insulation near the core outside the diameter.

The interlaminar insulation may be damaged during assembly or maintenance of a stator, particularly during the removal and replacement of its rotor. Hot spots may also be caused by foreign objects, usually metallic, or by general deterioration of the interlaminar insulation. The hot spots can, if undetected, increase in magnitude to the point of iron melting and/or damaging the adjacent insulation surrounding the copper conductors.

Stator cores can be tested for damage using a "thermovision" test. In this test the core is excited by a massive winding to full rated flux. By this method any hot spots on the teeth are readily detected with an infra-red camera scanning the bore. However, this test is unlikely to detect deep-seated faults unless more sophisticated temperature measurements are made.

One type of apparatus which is suitable for detecting such stator core hot spots is an Electro-magnetic Core Imperfection Detector ("EL-CID"). With EL-CID, the stator core is excited to only about 3 percent of the full rated flux in the core, which is sufficient to induce eddy currents to flow in the damage insulation areas. Because the current is very small, however, the heating is insignificant. The EL-CID test relies on the electromagnetic detection of the axial fault currents flowing through the damaged region.

A special pick-up coil in the sensing head, known as a chattock potentiometer, is used to measure the magneto motive force between the teeth to detect any fault currents. The output of the coil is amplified and phase-sensitive detected to yield a D.C. voltage proportional to the component of fault current in phase quadrature with the excitation current. The chattock coil signal is referenced in the phase sensitive signal processor to a constant signal derived from a reference coil which is maintained at one position in the stator. The purpose of the reference signal is to cancel out the chattock coil signal produced by the excitation field and thereby increase discrimination with respect to the fault currents.

Once a hot spot has been found using EL-CID, very standard industry procedures exist for restoring the interlaminar resistance of the punchings. Included are etching techniques and iron spreading for the addition of mica insulation with localized iron replacement as the solution for extreme insulation damaged areas.

To effectively use such EL-CID apparatus without disassemble of a generator, an effective system is necessary for positioning the EL-CID apparatus at appropriate test locations.

Additionally, other generator problems develop which can be detected by visual inspection of the stator of the generator. Due to the inaccessibility of the generator stator, without rotor removal, such visual inspection is best made when a camera is positioned in the vicinity of the generator stator which is to be inspected. Again, to be effective, it is necessary that some system properly position the camera within the generator.

Existing tests to perform the inspections described above are conducted manually and require removal of the generator rotor from within the stator. Rotor removal is a long and involved process. Removing the rotor, manually performing inspections and replacing the rotor can often consume 10 to 14 days. Removing a generator from service for such a period imposes serious problems on those relying on operation of the generator. Further, removing the rotor from the stator can itself cause damage to the stator. Also, replacing the rotor can damage the stator and a stator that has passed inspection may, therefore, become damaged after inspection, during rotor replacement.

Accordingly, there exists a need for an inspection system for an electric generator that does not require removal of the rotor from within the stator to perform the inspection and which does not require that the generator employ any particular type of baffle wedge groove to be functional.

SUMMARY OF THE INVENTION

The present invention provides a movable carriage which includes a chasis which is adapted for movement along a surface and magnets which are attached to the chasis for movably securing the chasis to the surface.

Also provided is a carriage positioning device which includes positioning apparatus which is adapted for releasable attachment to the carriage.

Additionally, a carriage assembly is provided which includes a carriage which is adapted for movement along a surface, positioning apparatus which is adapted for releasable attachment to the carriage and magnets which are attached to the carriage for removably attaching the carriage to the surface.

Also provided is an inspection system which includes a carriage which is adapted for movement along a surface, positioning apparatus which is adapted for releasable attachment to the carriage, magnets which are attached to the carriage for movably attaching the carriage to the surface and inspection apparatus mounted on the carriage for inspecting in the vicinity of the carriage.

Further, an electrical generator inspection system is provided which includes a carriage which is adapted for movement along a surface of an electrical generator, positioning apparatus which is adapted for releasable attachment to the electrical generator and the carriage, magnets which are attached to the carriage for movably attaching the carriage to the generator and the positioning means and inspection apparatus which is mounted on the carriage for inspecting the electrical generator in the vicinity of the carriage.

BRIEF DESCRIPTION OF THE DRAWINGS

The invention may be better understood, and further advantages and uses thereof are readily apparent, when considered in view of the following detailed description of exemplary embodiments, taken with the accompanying drawings in which:

FIG. 1 is a perspective view of the apparatus of the present invention;

FIG. 2 is a front elevational view of the apparatus of the present invention;

FIG. 3 is a side elevational view of the apparatus of the present invention;

DETAILED DESCRIPTION OF THE PREFERRED EMBODIMENT

Figure 4:
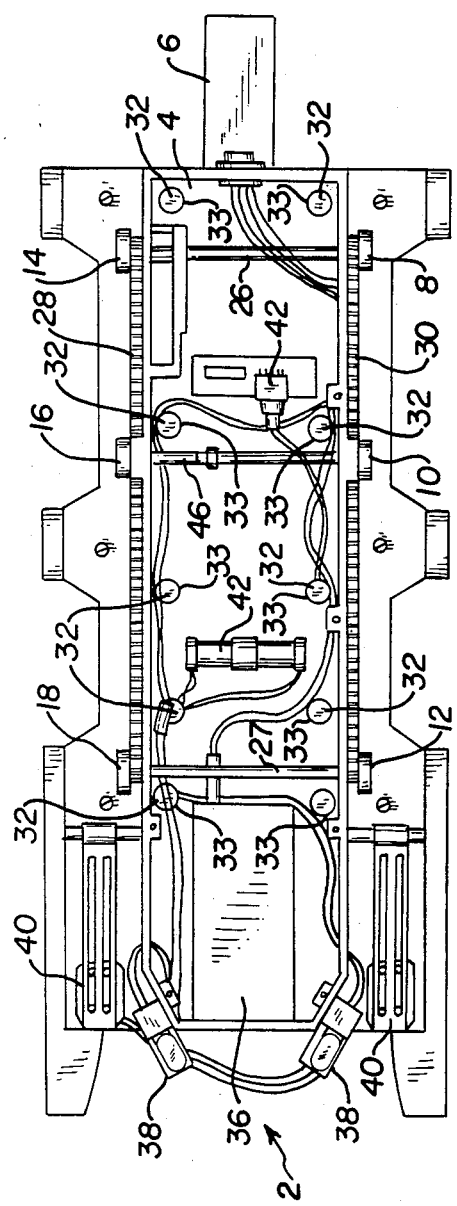
FIG. 4 is a top view of the apparatus of the present invention.

FIGS. 1 through 7 show inspection system 2 which comprises carriage 4 and positioning means 6. Carriage 4 moves relative to positioning means 6 by wheels 8, 10, 12, 14, 16 and 18. To facilitate the smooth movement of carriage 4, wheels 8, 10, 12, 14, 16 and 18 are mechanically interconnected to rotate at generally equal angular velocities. Wheels 8 and 14 are mechanically connected through axle 26, wheels 10 and 16 are mechanically connected through axle 46 while wheels 12 and 18 are mechanically connected through axle 27.

Additionally, to insure equal rotational velocity among those three pairs of wheel/axle assemblies, chains 28 and 30 are provided. Axles 26, 27 and 46 each include two mechanically attached, radially projecting sprockets (not shown), one adjacent each wheel. Chain 28, which is preferably sold by Winfred M. Berg of East Rockaway, N.J. as "FLEX-E-GEAR" Model No. GCF-50-E, engages the sprockets on axles 26, 27 and 46 adjacent wheels 14, 18 and 16, respectively, while chain 30 engages the sprockets on axles 26, 27 and 46 adjacent wheels 8, 12 and 10, respectively. With this arrangement, axles 26, 27 and 46 along with wheels 8, 10, 12, 14, 16 and 18 all rotate at generally the same angular velocity.

Chasis 5 of carriage 4 is preferably formed by machining a solid piece of nylon. Ten magnets 32 are positioned within recesses 33, which are formed in and positioned along the sides of carriage 4. Magnets 32 movably attach carriage 4 to the ferrous metal surface over which carriage 4 travels. When carriage 4 is placed on positioning means 6, magnets 32 are attracted to ferrous metal rails 34, which extend generally along the entire longitudinal length of positioning means 6 thereby holding carriage 4 in place. When carriage 4 is positioned within an electric generator and not on positioning means 6, magnets 32 are attracted to the ferrous metal internal parts of the generator thereby allowing carriage 4 to assume a variety of positions including being suspended from the bottom of a horizontal surface or the side of a vertical surface. Magnets 32 are high strength neodymium magnets, made by Bunting Magnetics of Newton, Kans., which collectively develop in excess of 20 pounds attraction to the stator of a generator. More or fewer magnets 32 may be used depending on the particular application.

Also positioned within carriage 4 is camera 36 which is preferably a Sony Model HVM-302 camera which is used for inspecting the interior of the generator. Due to the generally poor illumination within an electrical generator, lamps 38 are provided for illumination in the vicinity of camera 36. Also positioned on carriage 4 are EL-CID sensors 40. The construction and operation of EL-CID equipment is well known to those skilled in the art. Electrical components 42 are connected to EL-CID sensors 40 and form part of the overall EL-CID equipment. The operation and construction of electrical components 42 in conjunction with EL-CID sensors 40 are, likewise, well known to those skilled in the art.

Figure 5:
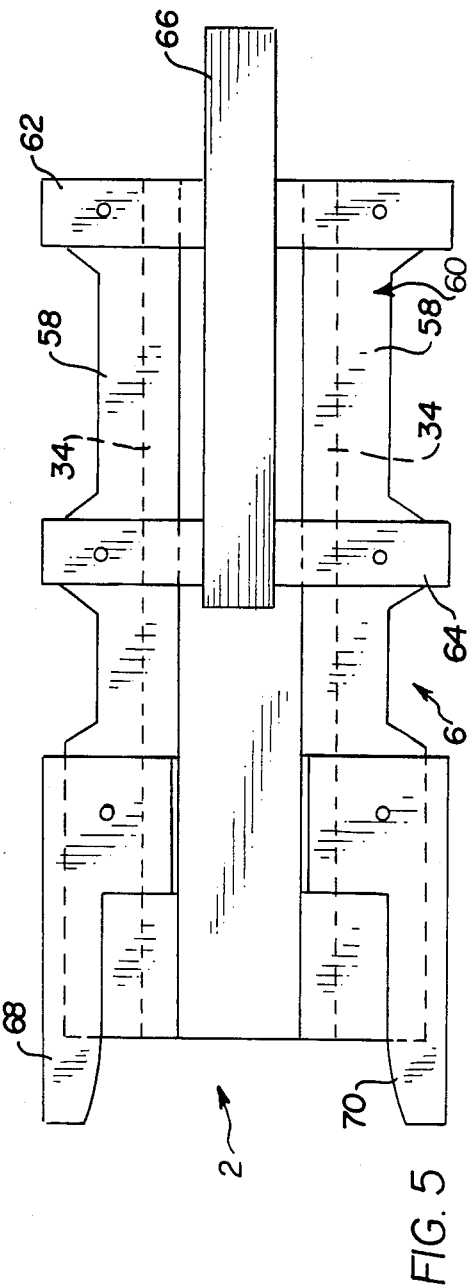
FIG. 5 is a bottom view of the positioning means of the apparatus of the present invention.

FIG. 5 shows a bottom view of positioning means 6. Positioning means 6 includes frame members 58 and 60. Frame members 58 and 60 are held in rigid relative position through the use of cross members 62 and 64. Handle 66, which is attached to cross members 62 and 64, provides a convenient means for placing positioning means 6 within the interior of a generator.

Figure 6:
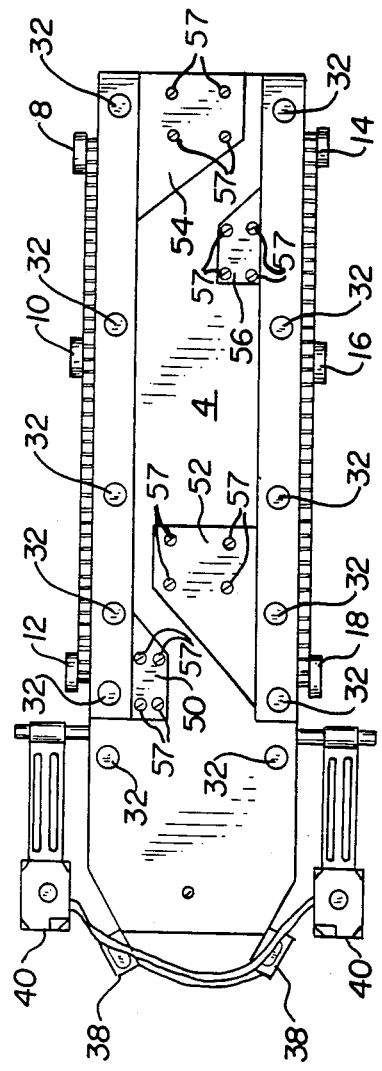
FIG. 6 is a bottom view of the carriage of the present invention.

FIG. 6 shows the bottom of carriage 4. Carriage 4 includes guides 50, 52, 54 and 56. Guides 50, 52, 54 and 56, which are preferably made of nylon or derlin, guide carriage 4 in perfect alignment with the stator slot. Guides 50, 52, 54 and 56 can be adjusted to accommodate all slot widths and depths, on current generators, by loosening screws 57 on each of the guides, moving the guides and then retightening screws 57 on each guide.

Figure 7:
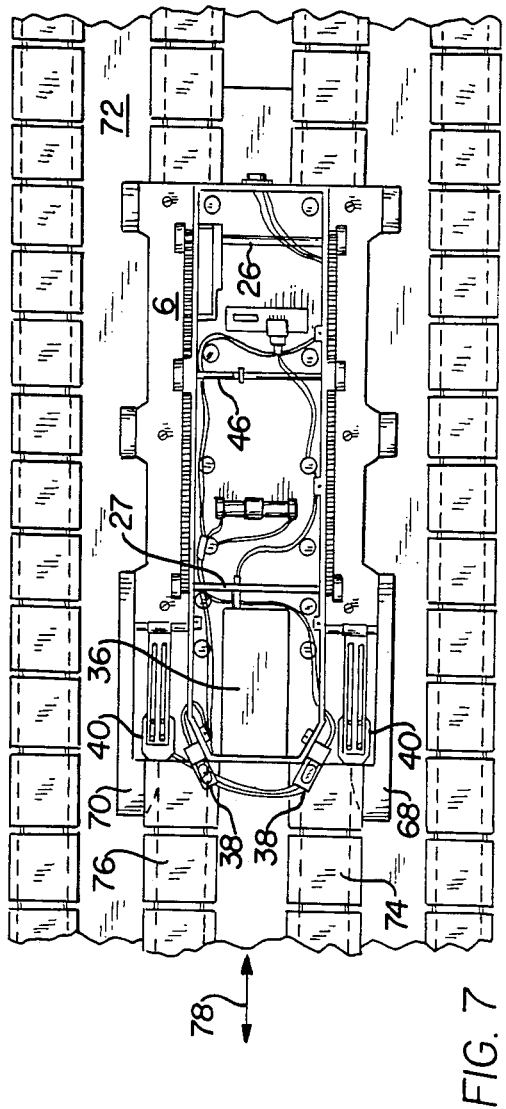
FIG. 7 is a top view of the apparatus of the present invention positioned on two stator teeth of an electrical generator.

As shown in FIGS. 1-4 and 7, carriage 4 mounts on positioning means 6. This entire assembly is then slid onto stator 72 of the electric generator (FIG. 7). Guides 68 and 70 engage teeth 74 and 76, respectively, of stator 72. Once positioned in this manner, carriage 4 may be rolled out of engagement with positioning means 6 on wheels 8, 10, 12, 14, 16 and 18. Since all of wheels 8, 10, 12, 14, 16 and 18 rotate at generally the same angular velocity and are of generally equal diameter, carriage 4 moves generally linearly along the path of arrow 78. Guides 50, 52, 54 and 56 also assist in this linear movement.

Magnets 32 are attracted to the ferrous surface of teeth 74 and 76 preventing carriage 4 from becoming disengaged from stator 72. As carriage 4 is maneuvered along the length of stator 72, EL-CID sensors 40 monitor fault currents due to shorted laminations as described above.

Additionally, camera 36 transmits a visual image of the generators components, which are in the vicinity of camera 36, back to a television monitor (not shown) so that defects which cannot be detected by the EL-CID equipment may be discovered. When visual inspection of the generator is performed with camera 36, it is preferable that lamps 38 be illuminated so that a proper image may be detected by camera 36.

A variety of means may be employed to move carriage 4 along path 78. For example, wheels 8, 10, 12, 14, 16 and 18 may be rotated by an electric motor whose use and operation are well known to those skilled in the art. Also, it is contemplated that carriage 4 may simply be attached to a long, generally straight rod or handle and manually moved. A variety of other means may be employed to move carriage 4 and such means are well known to those skilled in the art.

After inspection of the entire length of stator teeth 74 and 76 is performed, carriage 4 is returned to its original position on positioning means 6 and the entire assembly is removed from stator 72 through the use of handle 66. The entire assembly may then be repositioned on two other stator teeth which may then be inspected. This process may be continued until all teeth of stator 72 have been properly inspected.

It may be appreciated, therefore, that the apparatus of the present invention is useful in providing inspections of stators of electrical generators, including those which do not incorporate any particular form of air-gap baffle wedge groove. It may also be appreciated that the apparatus of the present invention may be used in conjunction with a variety of other apparatus, other than electrical generators, which employ ferrous metal surfaces to which the magnetic carriage may be movably attached.

Whereas particular embodiments of the invention have been described for purposes of illustration, it will be evident to those skilled in the art that numerous variations of the details may be made without departing from the invention as defined in the appended claims.

What is claimed is:

1. A moveable carriage comprising:
   chassis means adapted for movement along a surface;
   magnet means attached to said chasis means for moveably securing said chasis means to the surface; and
   separator means interposed between said magnet means and the surface for relatively positioning said magnet means out of contact with the surface.

2. The carriage of claim 1 wherein inspection means are mounted on said chasis means for inspecting in the vicinity of said carriage.

3. The carriage of claim 2 wherein said inspection means includes electrical generator inspection means.

4. The carriage of claim 3 wherein said electrical generator inspection means includes camera means.

5. The carriage of claim 3 wherein said electrical generator inspection means includes electro-magnetic core imperfection detector means.

6. The carriage of claim 4 including illumination means mounted on said chasis means.

7. A carriage positioning device for positioning a carriage with magnetic attachment apparatus comprising:
   positioning means adapted for releasable attachment to the carriage; and
   carriage securing means which includes magnetic attraction means for magnetically releasably securing the carriage to said positioning means.

8. The positioning device of claim 7 wherein said positioning means is adapted for releasable attachment to an electrical generator.

9. A carriage assembly comprising:
   a carriage adapted for movement along a surface;
   positioning means adapted for releasable attachment to said carriage; and
   magnet means attached to said carriage for moveably attaching said carriage to the surface.

10. The carriage assembly of claim 9 wherein said positioning means is adapted for releasable attachment to an electrical generator.

11. An inspection system comprising:
    a carriage adapted for movement along a surface;
    positioning means adapted for releasable attachment to said carriage;
    magnet means attached to said carriage for movably attaching said carriage to the surface; and
    inspection means mounted on said carriage for inspecting in the vicinity of said carriage.

12. The inspection system of claim 11 wherein said inspection means includes electrical generator inspection means.

13. The inspection system of claim 12 wherein said electrical generator inspection means includes camera means.

14. The inspection system of claim 12 wherein said electrical generator inspection means includes electro-magnetic core imperfection detector means.

15. The inspection system of claim 13 including illumination means mounted on said carriage.

16. An electrical generator inspection system comprising:
    a carriage adapted for movement along a surface of the electrical generator;
    positioning means adapted for releasable attachment to the electrical generator and said carriage;
    magnet means attached to said carriage for moveably attaching said carriage to the generator and said positioning means; and
    inspection means mounted on said carriage for inspecting the electrical generator in the vicinity of the carriage.

17. The electrical generator inspection system of claim 16 wherein said inspection means includes camera means.

18. The electrical generator inspection system of claim 16 wherein said inspection means includes electro-magnetic core imperfection detector means.

19. The electrical generator inspection system of claim 17 including illumination means mounted on said carriage.

* * * * *